United States Patent [19]

Stroetmann

[11] 4,427,650

[45] Jan. 24, 1984

[54] ENRICHED PLASMA DERIVATIVE FOR ADVANCEMENT OF WOUND CLOSURE AND HEALING

[75] Inventor: Michael Stroetmann, Münster, Fed. Rep. of Germany

[73] Assignee: Serapharm Michael Stroetmann, Münster, Fed. Rep. of Germany

[21] Appl. No.: 385,664

[22] Filed: Jun. 7, 1982

[30] Foreign Application Priority Data

Jun. 25, 1981 [DE] Fed. Rep. of Germany ....... 3124962
Dec. 18, 1981 [EP] European Pat. Off. ........... 81110615

[51] Int. Cl.$^3$ ...................... A61K 9/14; A61K 35/14; A61K 37/00
[52] U.S. Cl. ...................................... 424/46; 424/45; 424/101; 424/177
[58] Field of Search .................... 424/101, 177, 45, 46

[56] References Cited

U.S. PATENT DOCUMENTS 2,492,458 12/1949 Bering ................................. 424/101
4,298,598 11/1981 Schwarz et al. .................... 424/177
4,362,567 12/1982 Schwarz .............................. 424/101

OTHER PUBLICATIONS

McKendrick–Chem. Abst., vol. 76 (1972), p. 17809n.
Bruhn et al.–Chem. Abst., vol. 90 (1979), p. 101085v.
Schwarz et al.–Chem. Abst., vol. 94 (1981), p. 36384h.
Schwarz et al.–Chem. Abst., vol. 94 (1981), p. 36318q.

*Primary Examiner*—Sam Rosen
*Attorney, Agent, or Firm*—Gordon W. Hueschen

[57] ABSTRACT

A preparation for accelerated hemostasis and optimized biochemical control of wound closure ("tissue adhesive") consists only of solid, powdery, biologically active constituents and contains 60 to 96% by weight of fibrinogen, which is largely liberated from cryo-insoluble globulin, 0.05 to 5% by weight of a fibrinolysis inhibitor, and 0.1 to 15% by weight of thrombin and/or prothrombin. For use, this enriched plasma derivative may be applied in the form of a dry, powdery mixture immediately and directly onto the wound or in the area of operation, respectively. Further application methods provide atomizing, spraying, or foaming of the powdery mixture by means of a propellant.

13 Claims, No Drawings

ENRICHED PLASMA DERIVATIVE FOR ADVANCEMENT OF WOUND CLOSURE AND HEALING

The present invention relates to an enriched plasma derivative in the form of a biochemical substrate for accelerated hemostasis and optimum control of wound closure. In particular the invention relates to such a plasma derivative for advance would closure and wound healing containing 60 to 96% by weight of fibrinogen and 0.05 to 5% by weight of a fibrinolysis inhibitor.

It is the task of the blood coagulation system to form from certain plasma components, in particular from dissolved fibrinogen, insoluble fibrin and to deposit the same on the wound in order to stop bleeding chemically and mechanically. In the course of this hemostatis, fibrin forms a mechanically resistant closure of tissue and vascular injuries. On the other hand, together with the fibrinolytic system and the components of the coagulation system, fibrin constitutes the basis of the cellular "repair of tissue damage".

As has been shown by research results in the past ten years, the biochemical control of wound closure is a multi-stage catalytic process involving a multiplicity of forward and backward reactions or couplings, wherein a controlled coordination of the blood coagulation factors takes place, of which so far at least thirteen have been recognized and characterized. In addition to the coagulation factors, certain phospholipids as well as the factors of the thrombocytes are of a particular importance. The coagulation process itself is supported intravascularly by the endothelium.

The analytical clarification of the mechanisms of blood coagulation, the isolation of the factors and substances participating in the blood coagulation, the use of suitable supplementary materials and the development of suitable methods of application, offer to medical wound treatment the chance of an acceleration of hemostasis as well as of optimum control of wound closure. In particular, it has become possible to separate from natural plasma certain preparations, to store them and, when required, to apply them onto the wound together with further substances necessary for fibrin formation and interlacing in order to achieve controlled hemostasis.

In the art, a typical system of this kind is known by the term "fibrin adhesive". Therein, first a fibrinogen solution is applied onto the tissue parts to be adapted. Thereupon, small amounts of a highly concentrated thrombin and factor-XIII solution are dropped thereon for coagulation. A fibrinolysis inhibitor is added locally in order to prevent a premature lysis and thus the premature dehiscence of the adapted tissue parts. This technique causes great expenditure and is complicated due to the separate preparation, storage and application of the mentioned substances. Moreover, only a restricted spectrum of means (fibrinogen, thrombin, factor XIII, fibrinolysis inhibitor) is applied to the profile of requirements, viz., accelerated hemostasis and optimum wound closure.

Furthermore, from the German Laid-Open Patent Application No. 30 02 933 a tissue adhesive is known which, apart from small amounts of factor XIII and a fibrinolysis inhibitor such as aprotinin, consists of 60 to 98 parts of fibrinogen, 0.5 to 20 parts of cryo-insoluble globulin and 0 to 15 parts of albumin. This preparation is obtained from plasma cryoprecipitate by single or repeated treatment with a buffer solution and separation of cryo-soluble plasma protein. The obtained purified precipitate is dissolved and may be stored in this form at $-20°$ C. Alternatively, the dissolved purified precipitate may be preserved by deep-freezing. Also the product obtained after the lyophilization has to be reconstructed with aqua ad injectabilia prior to its use and accordingly is applied in liquid state. Additionally, a mixture of thrombin and calcium chloride has to be applied onto the tissue to be joined, which may be done either before application of the fibrinogen solution or simultaneously therewith.

In practice, the deep-frozen fibrinogen solution is thawed, thrombin and calcium chloride are added thereto, the mixture is kept for some time until the commencement of the polymerization reaction becomes noticeable by an increase of the viscosity, and this reacting mixture is applied onto the tissue parts to be joined. In many cases, the expenditure for preparing the tissue adhesive suitable for use and the short life of the tissue adhesive ready for use have proven to be an impediment. On the other hand, the application is difficult for the practising physician because he cannot reliably determine the short-time interval of a still-liquid adhesive.

On the basis thereof, it is the object of the present invention to provide a tissue adhesive in the form of an enriched plasma derivative which has practically unlimited storage stability at room temperature and is directly, i.e., without any change of its state of aggregation and without the addition of other necessary components, applicable onto the wound and the area of operation, respectively.

According to the present invention, this object is solved by a powdery biochemical substrate for accelerated hemostasis and optimized biochemical control of wound closure, viz., an enriched plasma derivative containing fibrinogen, thrombin, components of the prothrombin complex and protease inhibitors, all of them in dry, solid form. The composition of this powdery biochemical substrate is selected with regard to an optimized activation of the exogenic and/or endogenic coagulation system as well as under consideration of physiological and, if applicable, also pathological aspects. The complete tissue adhesive constitutes a powdery mixture exclusively made of dry, solid components, which has good storage stability and is directly applicable onto the wound and the area of operation, respectively, in this solid form.

In particular, the present invention provides for the solution of the above-specified object an enriched plasma derivative for supporting wound closure and wound healing, which contains 60 to 96% by weight of fibrinogen and 0.05 to 5% by weight of a fibrinolysis inhibitor, wherein (a) the fibrinogen is largely free from cryo-insoluble globulin;

(b) the plasma derivative additionally contains 0.1 to 15% by weight of thrombin and/or prothrombin;

(c) all components are present in biologically active, solid powdery form at temperatures of up to 56° C.; and (d) these solid components are mixed with each other.

This enriched plasma derivative according to the invention has practically unlimited storage stability, is rapidly soluble in the body fluids and, therefore, may immediately and directly be applied for wound closure without any further manipulation. Due to the admixture of thrombin and/or prothrombin, rapid polymerization occurs after partial passing into solution and/or dissolution in body fluid, and a viscous, well-adhering wound closing material is formed.

The powdery enriched plasma derivative according to the invention may be applied onto natural or synthetic carriers, the use of which permits a uniform distribution of the coagulation-active material on the wound surface. Furthermore, the powdery consistency of the preparation permits atomizing, spraying or foaming, whereby it is possible also to seal tissue fissures or cavities. Due to its dry, solid, powdery state, together with a combination of enzymes and proenzymes in the enriched plasma derivative, the storing thereof is particularly easy.

In contrast to the above-discussed known proposal, it has been recognized according to the invention that the fibrinogen isolated from human plasma shall largely be free from cryo-insoluble globulin. The presence of cryo-insoluble globulin impairs the fibrin formation and impedes the healing of the wound. Based on the total weight of the powdery enriched plasma derivative, the proportion of cryo-insoluble globulin shall be less than 2% by weight, preferably less than 0.4% by weight and most preferably less than 0.2% by weight. The less the proportion of cryo-insoluble globulin, the quicker will the fibrin polymerization start and take place.

Such a fibrinogen largely liberated from cryo-insoluble globulin may be obtained from human plasma by precipitation with a mixed solvent containing glycine, $\beta$-alanine and ethanol and subsequent dialysis and lyophilization of the precipitate. Preferably, the enriched plasma derivative according to the invention contains fibrinogen obtained in this manner. Such a fibrinogen has a molecular weight of $340,000 \pm 5\%$, is slightly partially digested in the $\alpha$-chain and is present in microcrystalline state. At room temperature, such a fibrinogen rapidly dissolves in body fluid and immediately thereupon starts to polymerize, e.g., in less than 2 min. The proportion of the fibrinogen which is coagulatable in solution shall amount to at least 85%. Such a fibrinogen is also called biologically active.

The enriched plasma derivative according to the invention contains 0.05 to 5% by weight of a fibrinolysis inhibitor. Preferably, one or several antiplasmins are used as the fibrinolysis inhibitor. Suitable antiplasmins, e.g., are aprothenin, $\alpha_1$-antiplasmin and/or trypsin inhibitor. The addition of such antiplasmins prevents the re-dissolution of the already-formed fibrin clot.

According to a further important aspect of the present invention, the enriched plasma derivative contains the solid, biologically active fibrinogen directly mixed with solid, biologically active prothrombin and/or thrombin. The proportion of thrombin and/or prothrombin shall amount to at least 0.1% by weight. In the case of lower proportions, the polymerization of the fibrinogen takes place with delay and incompletely. Thrombin and/or prothrombin proportions in excess of 15% by weight do not yield any additional effect and therefore are not advisable in view of the costs of such substances. Preferably, the proportion of thrombin and/or prothrombin shall amount to 1 to 10% by weight.

As is known, biologically active thrombin is used as a starting substance for the fibrin formation and reduces the reaction time of the fibrin conversion. Biologically active thrombin in the sense of this application will be present if its activity, under the known, standardized conditions, amounts to at least 1,000 international units per mg. Prothrombin is used as a thrombin reserve stable in storage, from which the latter forms when the powder is moistened. When introduced into body fluid, the prothrombin shall be convertible into thrombin to at least 95%.

Although the enriched plasma derivative according to the invention may contain either thrombin or prothrombin, the common presence of thrombin and prothrombin is preferred. Most preferably, 0.1 to 2 parts by weight of prothrombin shall be present per 1 part by weight of thrombin. The common presence ensures a high activity even after long-time storage even if high temperatures act thereon, e.g., may be valuable for the storage in the tropics. Furthermore, the combination of thrombin and prothrombin advances the direct conversion of prothrombin into thrombin upon moistening of the powdery mixture so that also coagulation factors formed at the wound, such as factor Xa, may contribute to the thrombin formation.

The specified system of fibrinogen, thrombin and/or prothrombin and fibrinolysis inhibitor, all in solid, powdery, biologically active form, constitutes a complete wound closure system, which is storable in dry form under sterile conditions for any length of time, but becomes biologically active after application onto the wound and the area of operation, respectively, by partially passing into solution and dissolution in the body fluid, where applicable, with cooperation of further factors contained in the body fluid. Preferably, this enriched plasma derivative forms a microcrystalline powdery mixture, consisting of 80 to 94% by weight of fibrinogen, 1 to 10% by weight of thrombin and/or prothrombin, and 0.01 to 3% by weight of the fibrinolysis inhibitor, wherein the content of cryo-insoluble globulin is less than 0.4% of the weight of the entire plasma derivative.

Although the specified components—fibrinogen, thrombin and/or prothrombin as well as fibrinolysis inhibitor, all of them in solid, powdery, biologically active form—form a complete, tissue adhesive suitable for application directly and immediately, i.e., without any further manipulation, the plasma derivative may additionally contain further constituents.

Preferably, phospholipids, prostaglandins, desiccating and stabilizing agents and/or blood coagulation factors, all of them in solid powdery form, are provided therefor. Well suited desiccating and stabilizing agents, e.g., are albumin or globulin, the latter, e.g., in the form of the commercially available mixture of $\alpha$-, $\beta$- and $\gamma$-globulin, or a mixture of albumin and globulin, albumin being used preferably. The proportion of albumin is not particularly critical and may be up to 35%, preferably up to 15% of the weight of the entire enriched plasma derivative. The presence of prostaglandins promotes the activation of the capillary bed in the areas of the wound as well as the activation of the platelets in the blood stream. The blood coagulation factors, e.g., factor XIII, blood platelet extracts and other factors necessary for blood coagulation such as, e.g., leucotrienes, platelet-activating factor, advance and increase the effect of the factors present in the body fluid in the sense of an accelerated hemostasis and an optimization of wound closure. As the phospholipid preferably a thrombocyte extract obtained from human full blood is used. Further suitable phospholipids, e.g., are extracts from cerebral substance. In view of their high specific effectiveness, the total of the proportions of prostaglandins, phospholipids and coagulation factors usually is not more than 1.2% by weight, preferably not more than 0.85% by weight, of the complete, enriched plasma derivative.

Furthermore, the enriched plasma derivative according to the invention may contain antibiotics and other additives effective in combating certain pathological conditions; these include, e.g., penicillin, antihistamines, vasopressins and coagulation factors XIII or IX for hemophilic wound healing.

The specified components of the enriched plasma derivative according to the invention for advancement of wound closure and healing are commercially available preparations or may be prepared according to known processes. Without limiting the invention thereto, respective processes for obtaining each of the essential components of the enriched plasma derivative according to the invention are specified in the following.

OBTAINING OF THE HUMAN FIBRINOGEN

Human plasma is cooled to 4° C. and $\beta$-alanine (2 molar solution in ethanol) is added thereto with agitation until the raw fibrinogen precipitates upon further ethanol addition. This raw fibrinogen is centrifuged off, dissolved in 0.01 M of tris buffer (pH 7.4), and again precipitated by adding 2 M of glycine. The isolated sediment is dissolved in a 0.9% aqueous NaCl solution, dialyzed relative to the same solvent, desalted and subsequently lyophilized.

The average molecular weight of the preparation thereby obtained is 340,000. After reduction with mercapto-ethanol, the $\alpha$-, $\beta$- and $\gamma$-chains are well detectable in gel electrophoresis. The molar extinction coefficient $E_{280}^{1\,cm}$ is 16.0. The extinction increase in the case of alkaline hydrolysis amounts to 12%. The proportion of cryo-insoluble globulin is less than 0.2% by weight, which may be determined by immuno-electrophoresis or radial-immuno-diffusion.

Furthermore, such commercially available fibrinogen preparations are especially suitable when, during the preparation thereof, care is taken to effect an extensive separation of the cryo-insoluble globulin. E.g., the product sold by the company Behring-Werke, Marburg, under the trade name Human Fibrinogen is a suitable solid, powdery human fibrinogen.

OBTAINING OF A COMBINED THROMBIN AND PROTHROMBIN PREPARATION

Prothrombin is either separated from commercially available prothrombin complex by column chromatography or extracted from the plasma by barium sulphate and recovered from the crystalline precipitate.

Additionally, thrombin and prothrombin are available commercially. E.g., thrombin in microcrystalline form with a biological activity of at least 3,000 units can be bought under the trade name "Topostasin" (from Hoffmann LaRoche, Grenzach, Baden). Analogously, prothrombin is obtainable as a PPSB preparation from the company Immuno AG, Vienna. Each of these commercially available preparations may be used for preparing the enriched plasma derivative according to the invention.

Suitable powdery fibrinolysis inhibitors are also commercially available.

aprotinin can be purchased from the company Behring-Werke, Marburg, or trasylol can be purchased from the company Bayer AG, Leverkusen, or $\epsilon$-aminocaproic acid can be purchased from typical fine-chemicals stores.

Furthermore, an antiplasmin suited as a fibrinolysis inhibitor, viz., $\alpha_1$-antiplasmin, can be obtained according to the following process.

OBTAINING OF $\alpha_1$-ANTIPLASMIN (FIBRINOLYSIS INHIBITOR)

Fibrinogen is covalently bonded to "Sepharose"* and converted into fibrin by thrombin. The thus-immobilized fibrin serves as a receptor for the plasmatic antiplasmin, which is bonded upon passage of plasma through the column and may be washed with $\epsilon$-aminocaproic acid.

* TM sepharose=agarose namely a linear polysaccharide of d-galactose and 3'6-anhydro-L-galactose Also the further constituents which, where applicable, are provided as further components (optional components) of the enriched plasma derivative according to the invention are commercially available such as, e.g., solid crystalline albumin (e.g., Behring-Werke, Marburg), powdery prostaglandin (e.g., Sigma-Chemie GmbH, Munich) as well as microcrystalline, biologically active coagulation factors (e.g., Immuno AG, Vienna).

An effective phospholipid may, e.g., be obtained according to the following prescription.

OBTAINING OF A PHOSPHOLIPID (PLATELET EXTRACT)

"Buffy coat" of a sediment from human full blood is exhaustively washed with Seiler solution (glucose-salt mixture) for separating the erythrocytes. The thus prepared leucocyte-monocyte-thrombocyte preparation is dissolved by adding Triton X ® (polyethylene glycol p-isooctylphenyl ether surface active agent), the insoluble portion is centrifuged off and the supernatant solution is fractionally precipitated with saturated ammonium sulphate at a pH of 7.4. The sediment is centrifuged off, dialyzed and dried. The phospholipid content of the fraction amounts to approx. 16 to 25%. When examined in the thromboplasmin test the preparation proves to be coagulation-active. The growth increase is examined by fibroplast increase in the culture.

Another suitable phospholipid may be obtained from cerebral substance by extraction with ether/chloroform.

Antibiotics and the like are commercially available preparations.

All of the above-mentioned preparations are solid at room temperature and at temperatures of up to 56° C. and substantially microcrystalline. The enriched plasma derivative according to the invention is obtained from these components by simple, dry mixing. E.g., the mixing may be carried out by treatment in a ball mill for 10 min. Alternatively, the mixing may be carried out by ultrasonic treatment and sieve classification. In each case, a dry, freely flowing powder is obtained from the homogeneous mixture of the constituents. In the following, compositions of preparations according to the invention are specified by way of examples, which are to be understood as non-limiting.

EXAMPLE 1

Enriched plasma derivative for advancement of wound closure and healing, consisting of 90 g of human fibrinogen (obtained according to the above-mentioned process), 0.5 g of thrombin (obtained from Behring-Werke, Marburg, biological activity at least 3,000 international units per mg),
0.5 g of trasylol (as fibrinolysis inhibitor, obtained from Bayer AG, Leverkusen),
0.7 g of phospolipid (obtained according to the above-mentioned process),
8.3 g of albumin (as desiccating and stabilizing agent, obtained from Behring-Werke, Marburg).

The mentioned solid, powdery materials were put into a ball mill and ground for 10 min. A homogeneous, freely flowing powder is obtained, which after sterilization treatment, e.g., with X-ray or gamma-ray radiation of a dose of 3 kW, can be applied, as an enriched plasma derivative for accelerated hemostasis and for advancement of wound closure and healing, directly onto the wound to be treated and in the area of operation, respectively.

TESTING OF THE THROMBIN ACTIVITY OF THE ENRICHED PLASMA DERIVATIVE

The dry powdery mixture according to example 1 was dissolved in a concentration of 0.5 mg of powdery mixture per 1 ml of 0.9% aqueous NaCl solution. 100 μl samples of this solution were tested with a standard solution of a chromogenic substrate (S2222 of the company Kabivitrum, Stockholm). In the end point analysis, the extinction increase at 405 nm must correspond to a thrombin activity of at least 0.001 international units. The system is calibrated with known amounts of thrombin so that it is easily possible to determine values lying therebetween.

In the present case, it was possible to prove 0.0025 to 0.003 units. The "units" have the meaning that 1 unit must cause 1 ml of a standardized fibrinogen solution to coagulate within 15 sec.

TESTING OF THE FIBRIN INTERLACING

The fibric clots formed by thrombin were immediately exhaustively washed in a 0.9% aqueous NaCl solution and thereupon dissolved in 0.1% monochloroacetic acid. The extinction value at 280 nm is used as a reference value. The clots later removed from the formulation at defined time intervals are less soluble. Their extinction values are compared with the zero value. After 30 min. at 37° C., the formed fibrin is no longer detectable in the specific solvent.

TESTING OF THE COAGULATION ACTIVITY OF THE ENRICHED PLASMA DERIVATIVE 10 mg portions of the dry powdery mixture according to example 1 were dissolved in a 5 mM CaCl$_2$ containing 0.9% aqueous NaCl solution with agitation. The coagulation activity of this solution was determined by the rate of the fibrin formation. For this purpose, samples were taken at defined time intervals and examined electrophoretically as to the proportions of fibrinogen and fibrinoligomers. Under the selected conditions, the coagulation time is 70 to 90 sec., wherein approx. 35% of the fibrinogen are converted into fibrinmonomers. The interlacing of the fibrin filaments by the factor XIII contained in the preparation is terminated within 30 min. Thereafter, the preparation can no longer be dissolved in 0.1% monochloroacetic acid.

EXAMPLE 2

The preparation of the powdery enriched plasma derivative was substantially analogous to example 1. Additionally, also 0.5 g of phospholipid from cerebral substance and 5,000 units of penicillin were added to the components of example 1 in the proportions specified therein. The mixing was carried out analogously to example 1.

10 mg portions of dry powdery mixture were dissolved in a 5 mM CaCl$_2$ containing 0.9% NaCl solution with rapid agitation. The fibrin formation commencing in the suspension may be observed through turbidity measurements. The gel electrophoresis is applied to detect the fibrinoligomers. As the dissolution of the powder coincides with the fibrin formation, the gelling of the formulation within the time of observance may be taken as a measure for the fibrin formation.

The addition of phospholipid from cerebral substance accelerates the coagulation of the flow of blood. The formulation is dissolved within 80 to 90 sec.

EXAMPLE 3

The preparation of the powdery mixture was substantially analogus to example 1. In contrast thereto, 65 g of human fibrinogen, 14.0 g of albumin and 18.7 g of globulin fraction (obtained from Behring-Werke, Marburg) were mixed with the other components of example 1 in the proportions specified therein.

10 mg portions of the obtained dry powdery mixture were dissolved in CaCl$_2$-containing 0.9% NaCl solution. The fibrin formation observed is slightly delayed (coagulation time 90 to 120 sec.), the formed gel is more plastic. Due to its elasticity, the fibrin cake may be applied, above all, in wound areas which are subjected to high mechanical stress by muscular force and contraction, e.g., in the case of deep skin wounds at extremities or in the case of tendon ruptures, which may be held together, after combing out of the collagen fibres, by means of the liquefying powder by the fibrinpolymers.

EXAMPLE 4

The preparation of the powdery mixture was substantially analogous to example 1. In contrast thereto, 96 g of human fibrinogen and 2.29 g of albumin were mixed with the other components of example 1 in the proportions specified therein. The fibrin clot formed from this plasma derivative proves to be stiffer, at least less elastic and extraordinarily pressure-stable. The wound closure is accelerated by the high fibrin concentration (coagulation time 50 to 70 sec.) so that this wound closing powder may be used in the case of more heavily bleeding traumas, ruptures of a vessel or skin injuries for which a high escape velocity of the capillary blood is characteristic.

EXAMPLE 5

Enriched plasma derivative for supporting wound closure and healing, consisting of 85% by weight of fibrinogen (commercially available preparation containing less than 2% by weight of cryo-insoluble globulin, obtained from Behring-Werke, Marburg);

4% by weight of thrombin ("Topostasin" from Hoffmann LaRoche, Grenzack, Baden; activity: at least 3,000 international units per mg);

5% by weight of prothrombin (PPSB-preparation, obtained from Immuno AG, Vienna);

1% by weight of fibrinolysis inhibitor, viz., a 1:1 mixture of $\alpha_1$-antiplasmin (prepared as specified above)

and α₂-macroglobulin (obtained from Behring-Werke, Marburg),

2% by weight of phospholipid from cerebral substance; for obtaining it, the meninges were removed from bovine or pig cerebral tissue, the tissue was washed so as to be free from blood, lyophilized and pulverized; the powder was extracted with chloroform/ether, the extract was concentrated by evaporation and the thus obtained residue was crushed and used;

3% by weight of globulin fraction (α-, β-, γ-globulin mixture, obtained from Böhringer, Mannheim).

Regarding the thrombin activity, the fibrin interlacing and the coagulation activity, the enriched plasma derivatives according to examples 2, 3, 4 and 5 yield results similar to those specified above in connection with example 1.

As already set out above, the enriched plasma derivative in the form of a dry powdery mixture, after the usual sterilization treatment, may be applied directly onto the tissue parts which are to be sealed or to the hemorrhage to be stopped. For this purpose, the powder may be sprinkled onto the moist place of application. Furthermore, the powdery enriched plasma derivative may be integrated in a first-aid bandage.

Another possibility of application is to apply the powdery mixture onto a biological carrier material such as, e.g., collagen, or onto a natural or synthetic dressing material and to apply this carrier and, respectively, dressing material provided with enriched plasma derivative. E.g., the dry powdery mixture may be blown onto absorbent gauze by means of a sterile gas jet. The dust-like powder adheres in sufficient amount to the large surface of the dressing material.

Suitable biological carrier materials for the application of the enriched plasma derivative, e.g., are collagen or fibrin. Commercially available collagen sponges or fibre structures as sold under the trade name "Kollagenvlies" by the companies Pentapharm or Hormonchemie are well suited. The dust-like powder firmly adheres in sufficient amount to such sponges. Preferably, approx. 0.5 mg of enriched plasma derivative is applied per cm² of carrier material surface. A collagen or fibrin fleece prepared in this manner may be used directly for wound treatment, or it may be integrated in a first-aid bandage (adhesive plaster).

The application of such biological carrier materials or natural or synthetic dressing materials enlarges the reaction surface and facilitates the covering of major wound areas.

According to a further, alternative application method, the enriched plasma derivative may be sprayed by means of a propellant which does not dissolve the plasma derivative. For this purpose, e.g., a spray may be provided which contains 100 mg of vacuum-dried enriched plasma derivative, e.g., the powdery mixture according to the above-specified example 1, in 10 ml of a suspension agent. E.g., an ethanol/ether mixture (8 parts by volume of ethanol per 2 parts by volume of ether) or "Frigen 114" ® (1,2-dichloro-1,1,2,2-tetrafluoroethane) may be used as the suspension agent. The suspension obtained is filled into a distributing can having a plunger-tongue atomizer screwed thereon.

A further form of application is that of a foam containing the enriched plasma derivative. For preparing such a foam, 100 mg of enriched plasma derivative, e.g., the powdery mixture according to the above-specified example 3, may be suspended in 10 ml of a carrier, e.g., a mixture of 1 part by volume of phospholipid and 9 parts by volume of glycerine, and this suspension may be foamed by means of carbon dioxide taken from ordinary $CO_2$ cartridges.

Atomizing of the powdery plasma derivative, spraying in the form of a spray, or foaming of a corresponding foam, permit the introduction into and sealing of poorly accessible tissue fissures and/or cavities.

Due to its solid state, the enriched plasma derivative according to the invention has excellent storage stability in the absence of moisture and can be stored for at least two years under dry, sterile conditions without losing more than 10% of its biological activity.

The biological activity in tissue sealing as well as the conversion into a hemostatic fibrin wound coating set in after the dry powdery plasma derivative has partially been passed into solution and been dissolved in body fluid. Already after a short time, e.g., after 2 min., there occurs an accelerated hemostatis. The biochemical control of the wound closure is increased and optimized by the increased offer of fibrinogen and fibrinolysis inhibitors. The adding of the platelet factors stimulates the coagulation of the escaping blood; the contained growth factors optimize the healing of the wound.

Any bleeding wound supplies coagulatable material which is swept away from the borders of the wound due to the flow velocity. Coagulatable, dry wound powders locally increase the coagulation potential, absorb liquid and promote the platelet adhesion. The collagen exposed in the area of the wound adsorbs the fibrin clot and increases the adhesion of the wound closing material. Due to the dry form of application, a special storing or a mixing with thrombin are unnecessary. The spray form makes the sealing of skin flaps, the safeguarding of operation sutures, or the prevention of seeping hemorrhages particularly easy.

It is to be understood that the invention is not to be limited to the exact details of operation or exact compounds, compositions, methods, or procedures shown and described, as obvious modifications and equivalents will be apparent to one skilled in the art.

I claim:

1. An enriched plasma derivative for supporting wound closure and healing, containing 60 to 96% by weight of fibrinogen and 0.5 to 5% by weight of a fibrinolysis inhibitor, wherein
   (a) the fibrinogen is largely free from cryo-insoluble globulin;
   (b) the plasma derivative additionally contains 0.1 to 15% by weight of thrombin and/or prothrombin;
   (c) all components are present in biologically active, solid powdery form at temperatures of up to 56° C.; and
   (d) these solid components are mixed with each other.

2. A plasma derivative as claimed in claim 1, wherein the fribrinogen is a product obtained from human plasma by precipitation with a mixed solvent containing glycine, β-alanine and ethanol and subsequent dialysis and lyophilization of the precipitate.

3. A plasma derivative as claimed in claim 1 or 2, wherein the fibrinogen contains less than 2% by weight of cryo-insoluble globulin.

4. A plasma derivative as claimed in claim 1 or 2, wherein the fibrinolysis inhibitor is an antiplasmin.

5. A plasma derivative as claimed in claim 1 or 2, wherein prothrombin is present and convertible into thrombin to at least 95%.

6. A plasma derivative as claimed in claim 1 or 2, wherein thrombin is present and has a biological activity of at least 1,000 international units per mg.

7. A plasma derivative as claimed in claim 1 or 2, wherein 0.1 to 2 parts by weight of prothrombin are provided per 1 part by weight of thrombin, both thrombin and prothrombin being present.

8. A plasma derivative as claimed in claim 1 or 2, wherein the plasma derivative contains 80 to 94% by weight of fibrinogen, 1 to 10% by weight of thrombin and/or prothrombin, 0.01 to 3% by weight of the fibrinolysis inhibitor, and less than 0.4% by weight of cryo-insoluble globulin.

9. A plasma derivative as claimed in claim 1, 2, or 8, wherein the plasma derivative substantially contains a phospholipid, a prostaglandin, a desiccating and stabilizing agent, an antibiotic and/or coagulation factor, all in solid, powdery form.

10. Method of using the enriched plasma derivative of claim 1, 2, or 8, wherein the dry, powdery mixture is applied directly onto a wound or in the area of an operation.

11. Method of claim 10, wherein the powdery mixture is provided on a biological carrier material.

12. Method of claim 11, wherein the biological carrier material is collagen or a natural or synthetic dressing material.

13. Method of claim 10, wherein the dry, powdery mixture is atomized, sprayed, or foamed in place by means of a propellant.

* * * * *

UNITED STATES PATENT AND TRADEMARK OFFICE
CERTIFICATE OF CORRECTION

PATENT NO. : 4,427,650
DATED : January 24, 1984
INVENTOR(S) : Michael Stroetmann It is certified that error appears in the above—identified patent and that said Letters Patent is hereby corrected as shown below:

Col. 1, line 18; "hemostatis," should read -- hemostasis, --

Col. 8, line 22; "analogus" should read -- analogous --

Col. 10, line 19; "hemostatis." should read -- hemostasis. --

Col. 10, line 57; "fribrinogen" should read -- fibrinogen --

Col. 11, line 15; delete "substantially" and insert -- additionally --

Signed and Sealed this

Eighteenth Day of September 1984

[SEAL]

Attest:

GERALD J. MOSSINGHOFF

Attesting Officer

Commissioner of Patents and Trademarks